US008602968B2

(12) United States Patent
Umemoto et al.

(10) Patent No.: US 8,602,968 B2
(45) Date of Patent: Dec. 10, 2013

(54) ENDOSCOPE APPARATUS

(75) Inventors: Yoshitaka Umemoto, Hachioji (JP);
Kazuhiko Takahashi, Hachioji (JP);
Tetsuo Nonami, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 573 days.

(21) Appl. No.: 12/559,828

(22) Filed: Sep. 15, 2009

(65) Prior Publication Data

US 2010/0004505 A1    Jan. 7, 2010

Related U.S. Application Data

(63) Continuation of application No. PCT/JP2008/055917, filed on Mar. 27, 2008.

(30) Foreign Application Priority Data

Mar. 29, 2007   (JP) .................................. 2007-089717

(51) Int. Cl.
*A61B 1/00* (2006.01)

(52) U.S. Cl.
USPC ........... 600/106; 600/117; 600/118; 600/145; 606/130; 318/568.11; 700/257

(58) Field of Classification Search
USPC .......................... 600/103, 104, 106; 606/130; 318/568.11, 568.24, 568.25; 700/257
See application file for complete search history.

(56) References Cited

U.S. PATENT DOCUMENTS

| | | | | |
|---|---|---|---|---|
| 5,675,229 A | * | 10/1997 | Thorne | .................... 318/568.11 |
| 5,876,325 A | * | 3/1999 | Mizuno et al. | ................ 600/102 |
| 6,292,712 B1 | * | 9/2001 | Bullen | .......................... 700/245 |
| 6,850,817 B1 | * | 2/2005 | Green | ........................... 700/245 |
| 7,074,179 B2 | * | 7/2006 | Wang et al. | .................... 600/101 |
| 7,194,335 B2 | * | 3/2007 | Sunaoshi | ...................... 700/254 |
| 2004/0068173 A1 | | 4/2004 | Viswanathan | |
| 2004/0186347 A1 | * | 9/2004 | Shose et al. | .................... 600/102 |
| 2005/0043719 A1 | * | 2/2005 | Sanchez et al. | ................... 606/1 |
| 2005/0096502 A1 | | 5/2005 | Khalili | |

(Continued)

FOREIGN PATENT DOCUMENTS

| | | |
|---|---|---|
| JP | 8-224248 | 9/1996 |
| JP | 10-230489 | 9/1998 |

(Continued)

OTHER PUBLICATIONS

JP 2004129782 For. Pat. and Machine Translation, Apr. 2004.*

(Continued)

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

When an operation instruction is input by a first (second) control output instruction input device, locus calculation means calculates a locus of movement of a first (second) therapeutic device on the basis of any one of joint sections, which is instructed to operate. On the basis of a calculation result by the locus calculation means, therapeutic device operation control means controls an operation of the first (second) therapeutic device by a first (second) active mechanism. Thereby, there is provided an endoscope apparatus which can improve the operational efficiency and positional precision of the therapeutic device.

9 Claims, 13 Drawing Sheets

(56) References Cited

U.S. PATENT DOCUMENTS

| | | | |
|---|---|---|---|
| 2005/0256371 A1* | 11/2005 | Schara et al. | 600/102 |
| 2006/0261770 A1* | 11/2006 | Kishi et al. | 318/568.11 |
| 2007/0260115 A1* | 11/2007 | Brock et al. | 600/114 |
| 2007/0287992 A1* | 12/2007 | Diolaiti et al. | 606/1 |
| 2008/0064921 A1* | 3/2008 | Larkin et al. | 600/104 |

FOREIGN PATENT DOCUMENTS

| | | | | |
|---|---|---|---|---|
| JP | 2000-316872 | | 11/2000 | |
| JP | 2001-046400 A | | 2/2001 | |
| JP | 2003-53684 | | 2/2003 | |
| JP | 2003-127076 | | 5/2003 | |
| JP | 2004-129782 | | 4/2004 | |
| JP | 2004129782 A | * | 4/2004 | A61B 19/00 |
| JP | 2004-223128 | | 8/2004 | |
| JP | 2008-119472 A | | 5/2008 | |
| JP | 2010-516371 A | | 5/2010 | |
| JP | 2010-518963 A | | 6/2010 | |
| WO | WO 2007/146987 A2 | | 12/2007 | |

OTHER PUBLICATIONS

Japanese Office Action dated Aug. 2, 2011 from corresponding Japanese Patent Application No. 2007-089717, together with English language translation.

English language abstract only of WO 2008103212 A2.

English language abstract only of WO 2008090484 A2.

European Search Report dated Oct. 24, 2012 from corresponding European Patent Application No. EP 08 73 9046.4.

\* cited by examiner

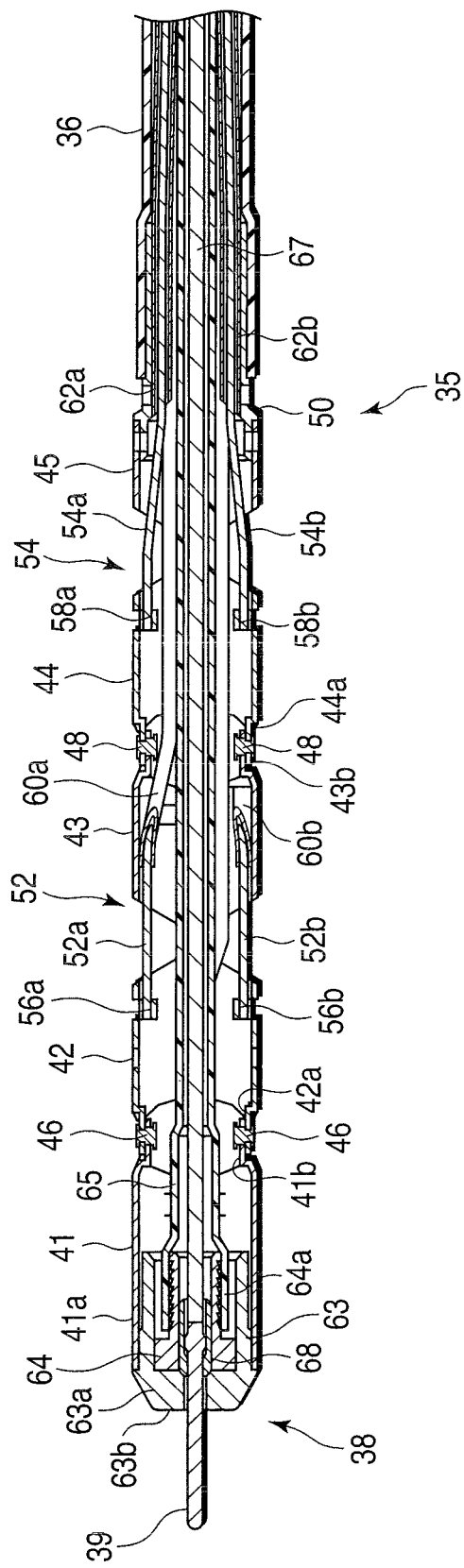
F I G. 6A

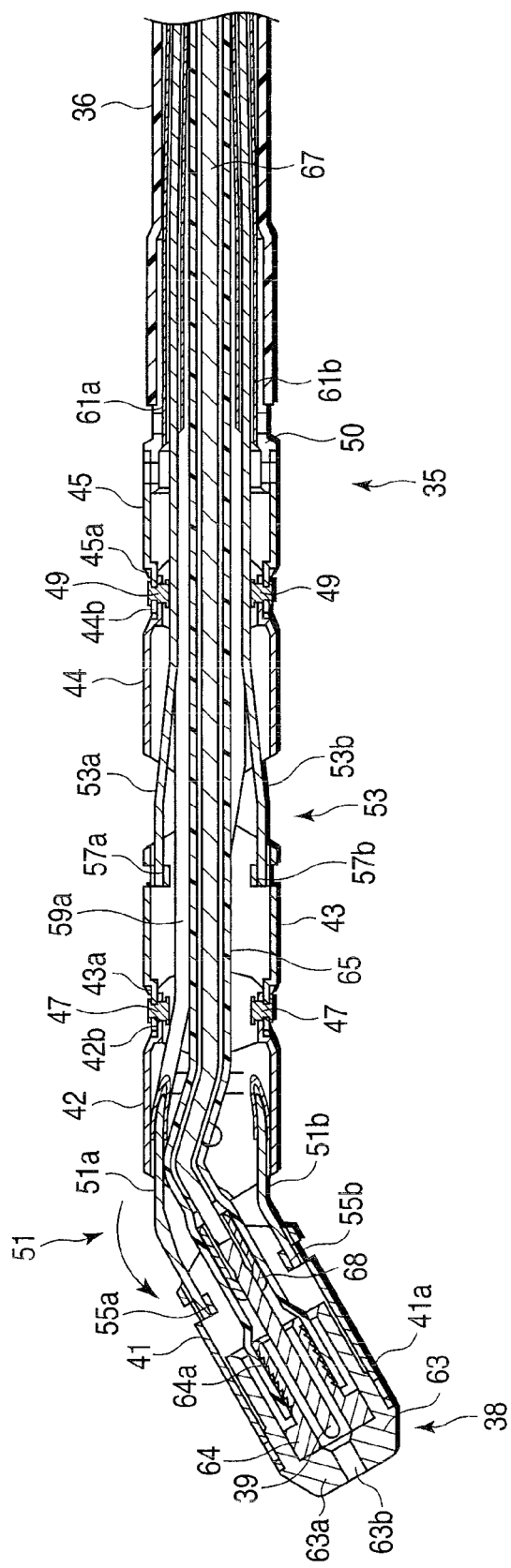
F I G. 6B

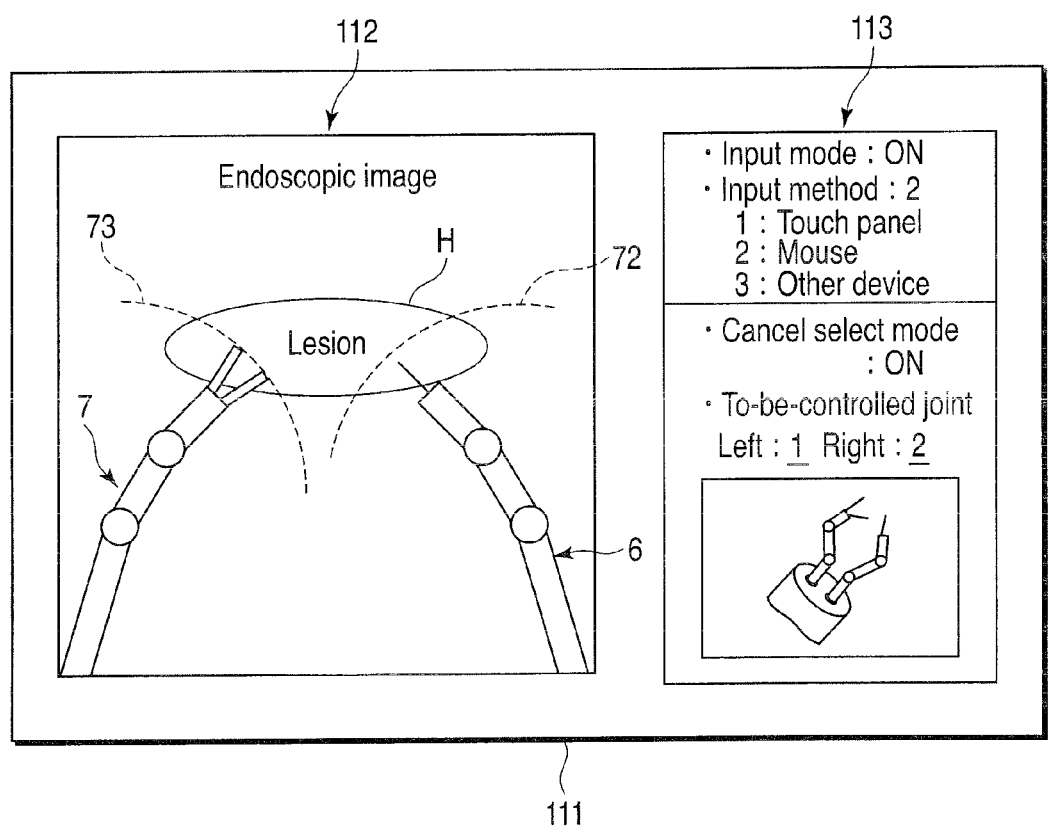
F I G. 15

ENDOSCOPE APPARATUS

CROSS-REFERENCE TO RELATED APPLICATIONS

This is a Continuation Application of PCT Application No. PCT/JP2008/055917, filed Mar. 27, 2008, which was published under PCT Article 21(2) in Japanese.

This application is based upon and claims the benefit of priority from prior Japanese Patent Application No. 2007-089717, filed Mar. 29, 2007, the entire contents of which are incorporated herein by reference.

BACKGROUND OF THE INVENTION

1. Field of the Invention

The present invention relates to an endoscope apparatus which performs diagnosis and therapeutic treatment of a lesion in a body cavity by using a therapeutic device which is inserted in a therapeutic device insertion channel of an endoscope.

2. Description of the Related Art

In general, diagnosis and therapeutic treatment of a lesion in a body cavity are performed by using a therapeutic device which is inserted in a therapeutic device insertion channel of an endoscope. In order to improve the operability of the therapeutic device, techniques for increasing the degree of freedom of the therapeutic device and for activating the therapeutic device have been studied.

Jpn. Pat. Appln. KOKAI Publication No. 2003-127076 (patent document 1), for instance, discloses a vertical multi-joint 6-degree-of-freedom robot which holds a scope so that the scope is movable to an arbitrary position. In this structure, the position and attitude of the scope are calculated from the angles of the respective joints of the arm of the vertical multi-joint 6-degree-of-freedom robot.

BRIEF SUMMARY OF THE INVENTION

According to a first aspect of the present invention, an endoscope apparatus comprising: an endoscope including at least an image pickup unit which captures an image in a subject, and a channel for therapeutic device insertion; a therapeutic device including an insertion section which is inserted in the subject via the channel of the endoscope, the insertion section including a plurality of joint sections which are capable of being independently and individually operated; operation means for operating the therapeutic device; instruction input means for inputting an operation instruction for operating the therapeutic device; locus calculation means for calculating a locus of movement of the therapeutic device on the basis of the joint section which is instructed to operate, when the operation instruction is input by the instruction input means; and therapeutic device operation control means for controlling an operation of the therapeutic device by the operation means on the basis of a calculation result by the locus calculation means.

In the above-described structure, when the operation instruction for operating the therapeutic device is input by the instruction input means, the locus calculation means calculates the locus of movement of the therapeutic device on the basis of the joint section which is instructed to operate. On the basis of the calculation result by the locus calculation means, the therapeutic device operation control means controls the operation of the therapeutic device by the operation means. Thereby, the locus of movement of the therapeutic device, which is based on the joint information of the joint that is arbitrarily selected, can be calculated, the driving control of the therapeutic device can be executed on the basis of the locus, and the multi-joint therapeutic device can efficiently be driven.

Preferably, the instruction input means includes working joint selection means for selecting a to-be-operated one of the plurality of joint sections, and the locus calculation means calculates the locus of movement of the therapeutic device on the basis of joint information of the joint which is selected by the working joint selection means.

In the above-described structure, the working joint selection means of the instruction input means selects the to-be-operated one of the plurality of joint sections, and the locus calculation means calculates the locus of movement of the therapeutic device on the basis of the joint information of the joint which is selected by the working joint selection means.

Preferably, the working joint selection means is a switching device for selecting one or more of the plurality of joint sections.

In the above-described structure, the switching device of the working joint selection means selects one or more of the plurality of joint sections.

According to second aspect of the present invention, an endoscope apparatus comprising: an endoscope including at least an image pickup unit which captures an image in a subject, and a channel for therapeutic device insertion; display means for displaying the image captured by the endoscope; a therapeutic device including an insertion section which is inserted in the subject via the channel of the endoscope, the insertion section including a plurality of joint sections which are capable of being independently and individually operated; operation means for operating the therapeutic device; instruction input means for inputting an operation instruction for operating the therapeutic device; locus drawing means for drawing a predetermined locus of movement of the therapeutic device on the display means on the basis of the joint section which is instructed to operate, when the operation instruction is input by the instruction input means; and therapeutic device operation control means for controlling an operation of the therapeutic device by the operation means with the joint section which is instructed to operate, on the basis of locus information of the locus which is drawn by the locus drawing means.

In the above-described structure, the locus drawing means draws the predetermined locus of movement of the therapeutic device on the display means on the basis of the joint section which is instructed to operate, when the operation instruction is input by the instruction input means. The therapeutic device operation control means controls the operation of the therapeutic device by the operation means with the joint section which is instructed to operate, on the basis of the locus information of the locus which is drawn by the locus drawing means.

Preferably, the therapeutic device operation control means includes working joint selection means for selecting the to-be-operated one of the plurality of joint sections on the basis of the locus information of the locus which is drawn by the locus drawing means, and therapeutic device operation control means controls the operation of the therapeutic device by the operation means on the basis of joint information of the joint which is selected by the working joint selection means.

In the above-described structure, the therapeutic device operation control means includes the working joint selection means for selecting the to-be-operated one of the plurality of joint sections on the basis of the locus information of the locus which is drawn by the locus drawing means, and the therapeutic device operation control means controls the operation of the therapeutic device by the operation means on the basis of the joint information of the joint which is selected by the working joint selection means.

Preferably, the locus drawing means includes calculation means for calculating at least one of a locus which is drawn by a distal end portion of the therapeutic device and a plane in which the distal end portion of the therapeutic device passes, and the locus drawing means draws, on the display means, one of the locus which is drawn by the distal end portion of the therapeutic device that is operated and the plane in which the distal end portion of the therapeutic device passes, on the basis of the joint section that is instructed to operate, when the operation instruction for operating the therapeutic device is input by the instruction input means.

In the above-described structure, the calculation means of the locus drawing means calculates at least one of the locus which is drawn by the distal end portion of the therapeutic device and the plane in which the distal end portion of the therapeutic device passes, and the locus drawing means draws, on the display means, one of the locus which is drawn by the distal end portion of the therapeutic device that is operated and the plane in which the distal end portion of the therapeutic device passes, on the basis of the joint section that is instructed to operate, when the operation instruction for operating the therapeutic device is input by the instruction input means.

Preferably, the instruction input means includes operation direction instruction input means for instructing and inputting an operation direction of a distal end portion of the therapeutic device on an endoscopic image which is displayed on a display screen of the display device, and the therapeutic device operation control means controls the operation of the therapeutic device by the operation means on the basis of an input by the operation direction instruction input means.

In the above-described structure, the operation direction instruction input means of the instruction input means instructs and inputs the operation direction of the distal end portion of the therapeutic device on the endoscopic image which is displayed on the display screen of the display device, and the therapeutic device operation control means controls the operation of the therapeutic device by the operation means on the basis of the input by the operation direction instruction input means. Thus, by calculating the to-be operated joint on the basis of the arbitrarily set locus, the driving control of the therapeutic device can be executed, and the multi-joint therapeutic device can efficiently be driven.

Preferably, the therapeutic device operation control device executes, on the basis of an input by the operation direction instruction input means, control to establish agreement between the operation direction of a distal end of the therapeutic device, the joint section which is selected by the working joint selection means and at least one of the locus of the distal end portion of the therapeutic device at this time and the plane in which the distal end of the therapeutic device passes, in association with the other joint sections of the therapeutic device which are not selected by the working joint selection means.

In the above-described structure, the therapeutic device operation control means executes, on the basis of the input by the operation direction instruction input means, control to establish agreement between the operation direction of the distal end of the therapeutic device, the joint section which is selected by the working joint selection means and at least one of the locus of the distal end portion of the therapeutic device at this time and the plane in which the distal end of the therapeutic device passes, in association with the other joint sections of the therapeutic device which are not selected by the working joint selection means.

BRIEF DESCRIPTION OF THE SEVERAL VIEWS OF THE DRAWING

FIG. 6A is a longitudinal cross-sectional view showing the state in which all joints of the multi-joint structure in the bending section of the knife-type therapeutic device of the first embodiment are set in a straight position;

FIG. 6B is a longitudinal cross-sectional view showing the state in which only the foremost joint is bent;

FIG. 15 is a front view showing a display screen of a monitor at a time of operating therapeutic devices of an endoscope apparatus according to a fourth embodiment of the present invention.

DETAILED DESCRIPTION OF THE INVENTION

Figure 1:
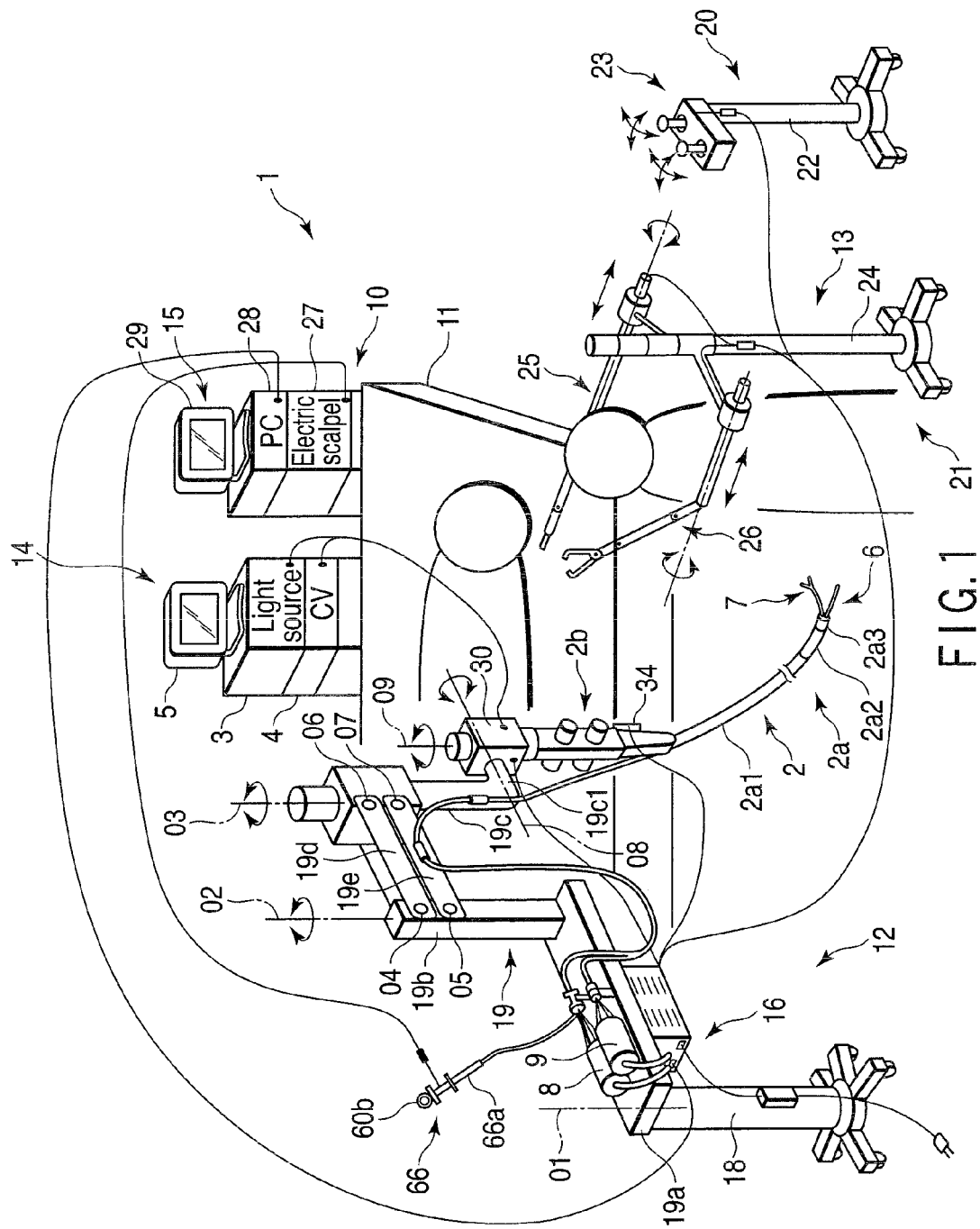
FIG. 1 schematically shows the structure of the entire system of an endoscope apparatus according to a first embodiment of the present invention.

A first embodiment of the present invention will now be described with reference to FIG. 1 to FIG. 9. FIG. 3 schematically shows the structure of the entire system of an endoscope apparatus 1 according to the present embodiment. The system of the endoscope apparatus 1 comprises an endoscope 2 and peripheral devices thereof. The peripheral devices include a light source device 3, a display processor 4, a display device 5, one or more (two (first and second) in the embodiment) active therapeutic devices 6 and 7, two (first and second) active mechanisms (operation means) 8 and 9, and a therapeutic device control unit 10. The light source device 3 generates endoscope illumination light. The display processor 4 is an image processing device which executes various image processes on image data which is captured by an image pickup unit of the endoscope 2. The first active mechanism 8 is a driving device of the first active therapeutic device 6, and the second active mechanism 9 is a driving device of the second active therapeutic device 7. The therapeutic device control unit 10 controls the operations of the first and second active therapeutic devices 6 and 7.

The first and second active therapeutic devices 6 and 7 are multi-joint type endoscopic therapeutic devices. The first active therapeutic device 6 is composed of, for instance, a radio-frequency knife of an electronic scalpel, and the second active therapeutic device 7 is composed of, for instance, a grasping forceps.

Figure 2:
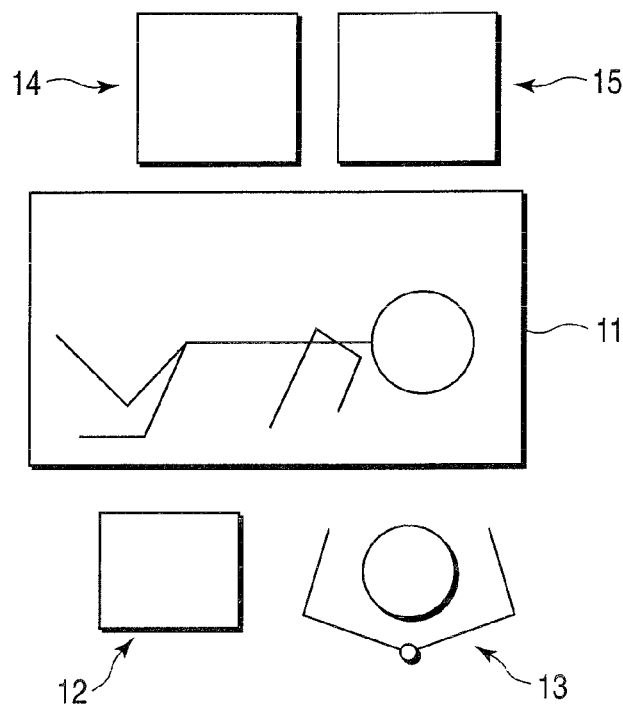
FIG. 2 schematically shows the structure of the entire system, illustrating the arrangement of the endoscope apparatus according to the first embodiment.
Figure 3:
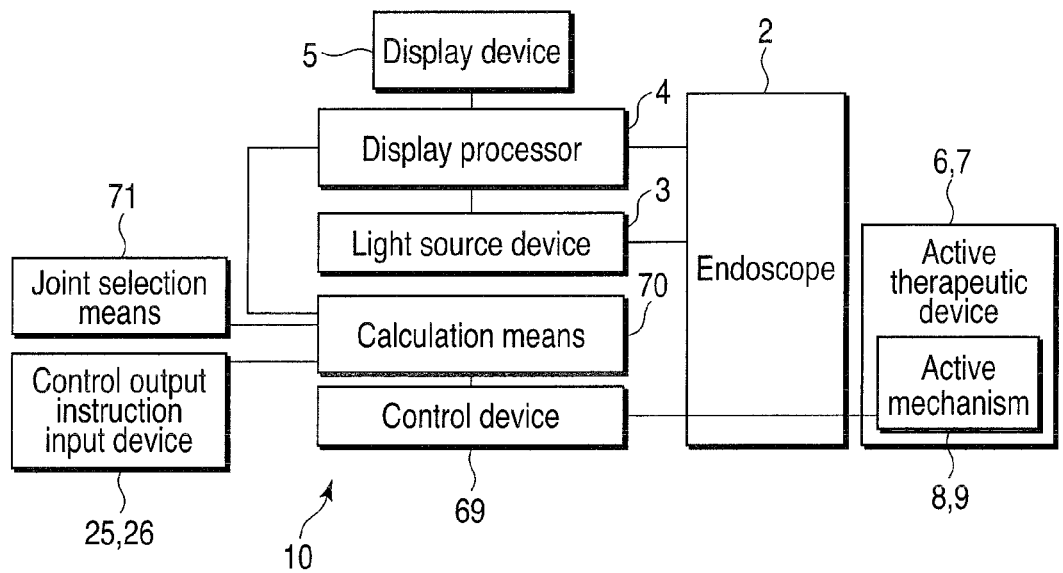
FIG. 3 is a block diagram of the entire system of the endoscope apparatus according to the first embodiment.

FIG. 1 and FIG. 2 show an example of actual use at a time when the system of the endoscope apparatus 1 according to the embodiment is installed in an operating room. In FIG. 2, an operation bed 11 is disposed at a central position. On one side of the operation bed 11, there are disposed a diagnosis/therapeutic device 12 for diagnosis and therapeutic treatment of a lesion in a body cavity, and an operation device 13 of the diagnosis/therapeutic device 12. On the other side of the operation bed 11, there are disposed an endoscope control device 14 and a therapeutic device control device 15.

The diagnosis/therapeutic device 12 includes an endoscope support device 16, the endoscope 2 that is supported by the endoscope support device 16, and the first and second active therapeutic devices 6 and 7. The endoscope support device 16 includes a floor stand 18, and a support arm 19 with a multi-stage arm structure.

The operation device 13 includes an endoscope operation unit 20 which operates the endoscope 2, and a therapeutic device operation unit 21. The endoscope operation unit 20 includes a stand 22, and an endoscope controller 23 which is mounted on the stand 22. The endoscope controller 23 is composed of, for example, a joystick which operates a bending operation of the endoscope 2. The therapeutic device operation unit 21 includes a stand 24, and first and second control output instruction input devices (instruction input means) 25 and 26 which are mounted on the stand 24. The first and second control output instruction input devices 25 and 26 are composed of master-type actuators of a master-slave system, which operate the first and second active therapeutic devices 6 and 7, respectively.

The endoscope control device 14 includes the light source device 3, the display processor 4 that is a camera control unit, and the display device 5. The therapeutic device control device 15 includes a control unit 27 of an electronic scalpel, a control unit 28 of a grasping forceps, and a display device 29 which displays control images of the first and second active therapeutic devices 6 and 7. A common monitor device may be used for the display device 5 of endoscopic images and the display device 29 of control images of the first and second active therapeutic devices 6 and 7.

The support arm 19 of the endoscope support device 16 includes a horizontal arm 19a, a first vertical arm 19b, a second vertical arm 19c, two (first and second) parallel link arms 19d and 19e, and an arm support body 19f. One end portion of the horizontal arm 19a is coupled to an upper end portion of the floor stand 18 in a manner to be rotatable about a first vertical axis O1. A lower end portion of the first vertical arm 19b is coupled to the other end portion of the horizontal arm 19a in a manner to be rotatable about a second vertical axis O2. The second vertical arm 19c is disposed parallel to the first vertical arm 19b. The first and second parallel link arms 19d and 19e are provided between the first vertical arm 19b and second vertical arm 19c. The arm support body 19f supports the second vertical arm 19c in a manner to be rotatable about a third vertical axis O3. The first and second active mechanisms 8 and 9 of the first and second active therapeutic devices 6 and 7 are disposed on the horizontal arm 19a.

One end portion of each of the first and second parallel link arms 19d and 19e is coupled to an upper end portion of the first vertical arm 19b in a manner to be rotatable about a horizontal axis O4, O5. The other end portion of each of the first and second parallel link arms 19d and 19e is coupled to the arm support body 19f in a manner to be rotatable about a horizontal axis O6, O7. Thus, the first vertical arm 19b, the first and second parallel link arms 19d and 19e and the arm support body 19f constitute a parallelogrammatic link which supports the second vertical arm 19c so as to be capable of vertical parallel movement.

A bent portion 19c1, which is bent in the horizontal direction, is formed at a lower end portion of the second vertical arm 19c. An endoscope holder 30 is supported on the bent portion 19c1 in a manner to be rotatable about a horizontal axis O8. A proximal end portion of the endoscope 2 is detachably supported on the endoscope holder 30 in a manner to be rotatable about a fourth vertical axis O9.

Figure 4A:
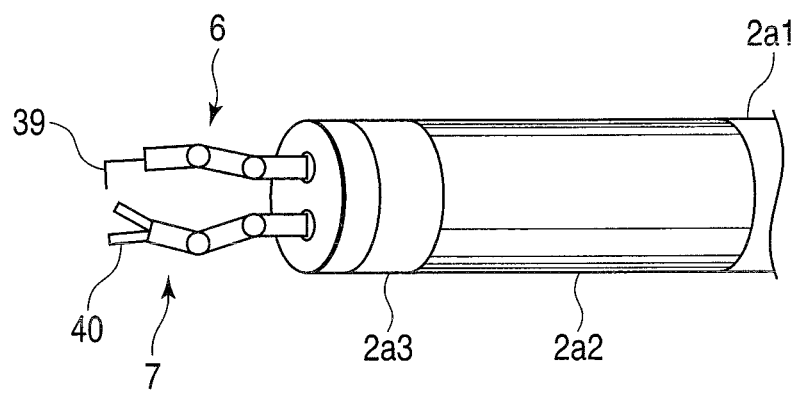
FIG. 4A is a perspective view showing the state in which two therapeutic devices are projected from an endoscope of the endoscope apparatus of the first embodiment.
Figure 4B:
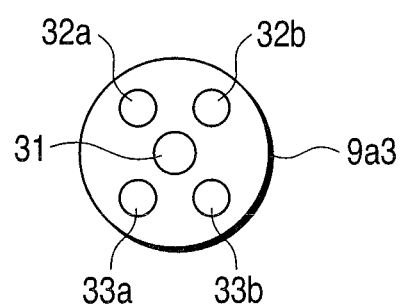
FIG. 4B is a front view showing a distal end face of the endoscope.

The endoscope 2 includes an elongated insertion section 2a which is to be inserted into the body, and a proximal-side end portion 2b which is coupled to a proximal end portion of the insertion section 2a. The insertion section 2a includes an elongated flexible tube portion 2a1, a bending section 2a2 which is coupled to a distal end of the flexible tube portion 2a, and a distal-end rigid portion 2a3 which is coupled to a distal end of the bending section 2a2. As shown in FIG. 4B, a distal end face of the distal-end rigid portion 2a3 is provided with, for example, one observation window portion 31, two illumination window portions 32a and 32b, and opening portions of two therapeutic device insertion channels 33a and 33b. On the inside of the observation window portion 31, there is disposed an image pickup unit (not shown) including an optical system such as an objective lens, and an image pickup element such as a CCD. A lesion in a body cavity, for instance, is imaged by the image pickup unit. An image pickup signal, which is obtained by the image pickup unit of the endoscope 2, is sent to the display processor 4 over a connection cable, and is converted to a video signal. By this video signal, an image that is captured by the endoscope 2 is displayed on the display device 5.

The bending section 2a2 is remotely bend-operated by tilt-operating the joystick of the endoscope controller 23. By bending the bending section 2a2, a desired observation object (e.g. lesion) can be captured within an observation visual field (or an image pickup visual field).

Two channel ports, which communicate with two therapeutic device insertion channels 33a and 33b, are formed near a coupling part between the proximal-side end portion 2b and insertion section 2a. The first and second active therapeutic devices 6 and 7 are inserted in the channel ports.

In the structure of the present embodiment, the first and second active therapeutic devices 6 and 7 are inserted into the two insertion channels 33a and 33b, respectively, in a one-to-one correspondence. Alternatively, a plurality of endoscopic therapeutic devices may be inserted in one insertion channel.

In addition, the proximal-side end portion 2b is provided with bend operation means 34, such as a joystick or a cross key, which bends the bending section 2a2.

The first active therapeutic device 6 and the second active therapeutic device 7 have main parts of substantially the same structure. In the description below, the structure of the first active therapeutic device 6 is described with reference to FIG. 5 to FIGS. 7A and 7B. The parts of the second active therapeutic device 7, which are common to those of the first active therapeutic device 6, are denoted by like reference numerals. A description of the common parts is omitted, and only different parts are described.

Figure 5:
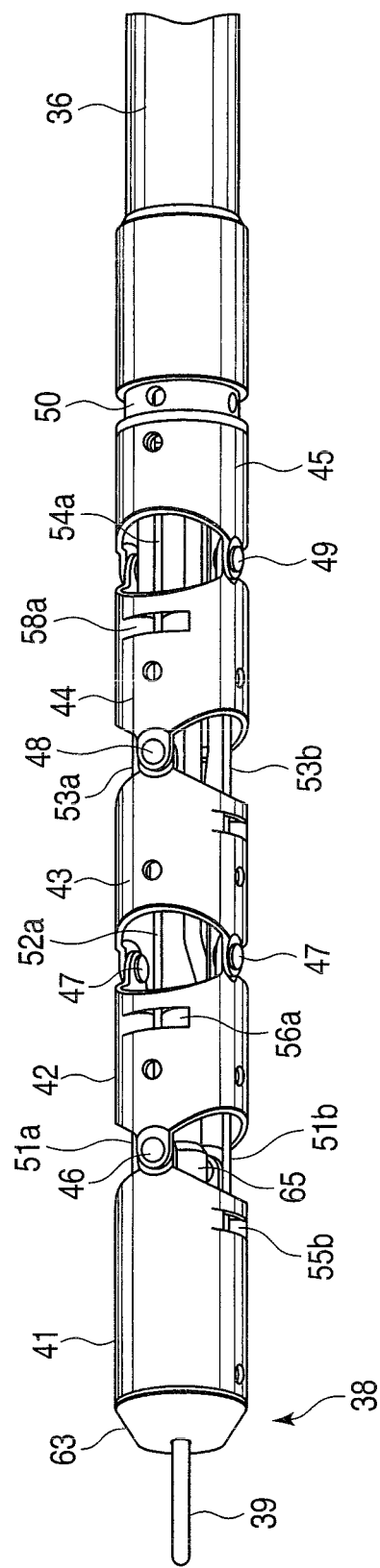
FIG. 5 is a perspective view showing a multi-joint structure in a bending section of a knife-type therapeutic device of the endoscope apparatus of the first embodiment.

As shown in FIG. 5, the first active therapeutic device 6 includes an elongated insertion section 35 which is inserted in the insertion channel 33a of the endoscope 2. The first active mechanism 8 is coupled to a proximal end portion of the insertion section 35. The insertion section 35 comprises an elongated flexible tube (flexible section) 36 which is disposed on the proximal side, a bending section 37 which is connected to a distal end of the flexible tube 36, and a distal-end therapeutic section 38 which is connected to a distal end of the bending section 37.

The flexible tube 36 is a flexible part which can resiliently be bent relatively softly by external force. The bending section 37 is a part which is forcibly bent by the first active mechanism 8. The distal-end therapeutic section 38 has a therapeutic function corresponding to the first active therapeutic device 6. In the present embodiment, a radio-frequency knife 39 is provided as the therapeutic function. In the second active therapeutic device 7, the distal-end therapeutic section 38 is provided with a grasping forceps 40.

As shown in FIG. 5, the bending section 37 includes a multi-joint type bending mechanism which is composed of a plurality of bend pieces (joint pieces) 41 to 45. Each of the bend pieces 41 to 45 is formed of an annular member. The bend pieces 41 to 45 are coaxially arranged and disposed in line in the axial direction of the insertion section 35. The bend pieces are referred to as a first bend piece 41, a second bend piece 42, a third bend piece 43, a fourth bend piece 44 and a fifth bend piece 45, in the named order from the distal end side.

A distal-end therapeutic section fixing portion 41a, to which the distal-end therapeutic section 38 is fixed, is provided at a front end portion of the first bend piece 41. Two tongue-shaped rearward projection portions 41b are projectingly provided on a rear end portion of the first bend piece 41. The two rearward projection portions 41b are disposed at positions of 180° in the circumferential direction of the first bend piece 41.

Two tongue-shaped forward projection portions 42a are projectingly provided on a front end portion of the second bend piece 42. Two tongue-shaped rearward projection portions 42b are projectingly provided on a rear end portion of the second bend piece 42. The two forward projection portions 42a and the two rearward projection portions 42b are disposed at positions of 180° in the circumferential direction of the second bend piece 42. In addition, the two forward projection portions 42a and the two rearward projection portions 42b are disposed at positions with a displacement of 90° from each other in the circumferential direction of the second bend piece 42.

The two rearward projection portions 41b of the first bend piece 41 and the two forward projection portions 42a of the second bend piece 42 are overlapped with each other and are rotatably coupled by first rotational shafts 46 which penetrate both portions 41b and 42a. The first rotational shafts 46 are rivet-shaped shaft members.

The third bend piece 43 and fourth bend piece 44 are structured like the second bend piece 42. Specifically, two tongue-shaped forward projection portions 43a are projectingly provided on a front end portion of the third bend piece 43, and two tongue-shaped rearward projection portions 43b are projectingly provided on a rear end portion of the third bend piece 43. The two forward projection portions 43a and the two rearward projection portions 43b are disposed at positions with a displacement of 90° from each other in the circumferential direction of the third bend piece 43. Two tongue-shaped forward projection portions 44a are projectingly provided on a front end portion of the fourth bend piece 44, and two tongue-shaped rearward projection portions 44b are projectingly provided on a rear end portion of the fourth bend piece 44. The two forward projection portions 44a and the two rearward projection portions 44b are disposed at positions with a displacement of 90° from each other in the circumferential direction of the fourth bend piece 44.

The two rearward projection portions 42b of the second bend piece 42 and the two forward projection portions 43a of the third bend piece 43 are overlapped with each other and are rotatably coupled by second rotational shafts 47 which penetrate both portions 42b and 43a. The second rotational shafts 47 are rivet-shaped shaft members. Similarly, the two rearward projection portions 43b of the third bend piece 43 and the two forward projection portions 44a of the fourth bend piece 44 are overlapped with each other and are rotatably coupled by third rotational shafts 48 which are rivet-shaped shaft members and penetrate both portions 43b and 44a.

Two tongue-shaped forward projection portions 45a are projectingly provided on a front end portion of the fifth bend piece 45. The two forward projection portions 45a are disposed at positions of 180° in the circumferential direction of the fifth bend piece 45. The two rearward projection portions 44b of the fourth bend piece 44 and the two forward projection portions 45a of the fifth bend piece 45 are overlapped with each other and are rotatably coupled by fourth rotational shafts 49 which are rivet-shaped shaft members and penetrate both portions 44b and 45a.

A front end portion of a circular cylindrical coupling member 50 is fitted and fixed to a rear end portion of the fifth bend piece 45. A rear end portion of the coupling member 50 is coupled and fixed to the flexible tube 36 in the state in which a distal end portion of the flexible tube 36 is fitted over the rear end portion of the coupling member 50.

Four wire units 51 to 54 for individually rotating the first bend piece 41 through the fourth bend piece 44 are provided in the insertion section 35. Each of the wire units 51 to 54 is composed of a pair of inextensible operation wires.

The first bend piece 41 is driven by two operation wires 51a and 51b of the first wire unit 51. Similarly, the second bend piece 42 is driven by two operation wires 52a and 52b of the second wire unit 52, the third bend piece 43 is driven by two operation wires 53a and 53b of the third wire unit 53, and the fourth bend piece 54 is driven by two operation wires 54a and 54b of the fourth wire unit 54.

As shown in FIG. 6B, two cut-and-raised portions 55a and 55b, which project inward, are formed on a peripheral wall surface of the rear end portion of the first bend piece 41. The two cut-and-raised portions 55a and 55b are disposed at positions of 180° in the circumferential direction of the first bend piece 41, and are disposed with a displacement of 90° from the two rearward projection portions 41b in the circumferential direction of the first bend piece 41. A distal end portion of one operation wire 51a of the first wire unit 51 is inserted in one cut-and-raised portion 55a, and is fixed by soldering. A distal end portion of the other operation wire 51b of the first wire unit 51 is inserted in the other cut-and-raised portion 55b, and is fixed by soldering.

Similarly, two cut-and-raised portions 56a and 56b (see FIG. 6A), which project inward, are formed on a peripheral wall surface of the rear end portion of the second bend piece 42. Two cut-and-raised portions 57a and 57b (see FIG. 6B), which project inward, are formed on a peripheral wall surface of the rear end portion of the third bend piece 43. Two cut-and-raised portions 58a and 58b (see FIG. 6A), which project inward, are formed on a peripheral wall surface of the rear end portion of the fourth bend piece 44. The two cut-and-raised portions 56a and 56b of the second bend piece 42 are disposed at positions of 180° in the circumferential direction of the second bend piece 42, and are disposed with a displacement of 90° from the two rearward projection portions 42b in the circumferential direction of the second bend piece 42. The two cut-and-raised portions 57a and 57b of the third bend piece 43 are disposed at positions of 180° in the circumferential direction of the third bend piece 43, and are disposed with a displacement of 90° from the two rearward projection portions 43b in the circumferential direction of the third bend piece 43. The two cut-and-raised portions 58a and 58b of the fourth bend piece 44 are disposed at positions of 180° in the circumferential direction of the fourth bend piece 44, and are disposed with a displacement of 90° from the two rearward projection portions 44b in the circumferential direction of the fourth bend piece 44.

A distal end portion of one operation wire 52a of the second wire unit 52 is inserted in one cut-and-raised portion 56a of the second bend piece 42, and is fixed by soldering. A distal end portion of the other operation wire 52b of the second wire unit 52 is inserted in the other cut-and-raised portion 56b, and is fixed by soldering.

A distal end portion of one operation wire 53a of the third wire unit 53 is inserted in one cut-and-raised portion 57a of the third bend piece 43, and is fixed by soldering. A distal end portion of the other operation wire 53b of the third wire unit 53 is inserted in the other cut-and-raised portion 57b, and is fixed by soldering.

A distal end portion of one operation wire 54a of the fourth wire unit 54 is inserted in one cut-and-raised portion 58a of the fourth bend piece 44, and is fixed by soldering. A distal end portion of the other operation wire 54b of the fourth wire unit 54 is inserted in the other cut-and-raised portion 58b, and is fixed by soldering.

The operation wires 51a, 51b, 52a, 52b, 53a, 53b, 54a and 54b are advancibly/retractably inserted in flexible guide sheaths 59a, 59b, 60a, 60b, 61a, 61b, 62a and 62b, respectively. The guide sheaths 59a, . . . , are formed of sheath-shaped flexible members, such as closely-wound coils or resin tubes. Each operation wire 51a, . . . , is guided by the inner hole of the associated flexible member only in the direction of advancement/retraction.

Specifically, the two operation wires 51a and 51b of the first wire unit 51 are advancibly/retractably inserted in the guide sheaths 59a and 59b. Distal end portions of the guide sheaths 59a and 59b are fixed to the inner peripheral surface of the front end portion of the second bend piece 42.

The two operation wires 52a and 52b of the second wire unit 52 are advancibly/retractably inserted in the guide sheaths 60a and 60b. Distal end portions of the guide sheaths 60a and 60b are fixed to the inner peripheral surface of the front end portion of the third bend piece 43.

The two operation wires 53a and 53b of the third wire unit 53 are advancibly/retractably inserted in the guide sheaths 61a and 61b. Distal end portions of the guide sheaths 61a and 61b are fixed to the inner peripheral surface of the front end portion of the coupling member 50. Alternatively, the distal end portions of the guide sheaths 61a and 61b may be fixed to the inner peripheral surface of the front end portion of the fourth bend piece 44 or the fifth bend piece 45.

The two operation wires 54a and 54b of the fourth wire unit 54 are advancibly/retractably inserted in the guide sheaths 62a and 62b. Distal end portions of the guide sheaths 62a and 62b are fixed to the inner peripheral surface of the front end portion of the coupling member 50. Alternatively, the distal end portions of the guide sheaths 62a and 62b may be fixed to the inner peripheral surface of the front end portion of the fifth bend piece 45.

The guide sheaths 59a and 59b are inserted from the inside of the second bend piece 42, successively into the third bend piece 43, fourth bend piece 44, fifth bend piece 45, coupling member 50 and flexible tube 36, and guided to the proximal-side first active mechanism 8.

The guide sheaths 60a and 60b are inserted from the inside of the third bend piece 43, successively into the fourth bend piece 44, fifth bend piece 45, coupling member 50 and flexible tube 36, and guided to the proximal-side first active mechanism 8.

The guide sheaths 61a and 61b and the guide sheaths 62a and 62b are inserted successively into the coupling member 50 and flexible tube 36, and guided to the proximal-side first active mechanism 8. Thereby, the respective operation wires 51a, 51b, 52a, 52b, 53a, 53b, 54a and 54b are individually guided to the proximal-side first active mechanism 8 through the different flexible guide sheaths 59a, 59b, 60a, 60b, 61a, 61b, 62a and 62b.

By individually and independently driving the four wire units 51 to 54, the first bend piece 41 through the fourth bend piece 44 can individually be rotated. Specifically, by pushing and pulling the two operation wires 51a and 51b of the first wire unit 51, only the first bend piece 41 can individually and independently be rotated about the first rotational shafts 46 and can individually be bent. Thus, a first joint section A1 is formed. Similarly, only the second bend piece 42 can individually and independently be rotated about the second rotational shafts 47 and can individually be bent by the two operation wires 52a and 52b of the second wire unit 52. Thus, a second joint section A2 is formed. Only the third bend piece 43 can individually and independently be rotated about the third rotational shafts 48 and can individually be bent by the two operation wires 53a and 53b of the third wire unit 53. Thus, a third joint section A3 is formed. Furthermore, only the fourth bend piece 44 can individually and independently be rotated about the fourth rotational shafts 49 and can individually be bent by the two operation wires 54a and 54b of the fourth wire unit 54. Thus, a fourth joint section A4 is formed. In this manner, in the present embodiment, the multi-joint type bending mechanism is formed, which can individually and independently drive the four joints of the first joint section A1, second joint section A2, third joint section A3 and fourth joint section A4. The parts of the multi-joint type bending mechanism are covered with a soft outer sheath (not shown), and constitute, as a whole, the bending section 37.

The distal-end therapeutic section 38 is provided with a bottomed cylindrical stopper member 63, a tubular coupling member 64 which is fixed in the stopper member 63, and the above-described radio-frequency knife 39. A radio-frequency knife insertion hole 63b is formed in an axial center portion of a distal-end closing portion 63a of the stopper member 63. The inside diameter of the coupling member 64 is made greater than that of the radio-frequency knife insertion hole 63b of the stopper member 63.

A rear end portion of the coupling member 64 is provided with a small-diameter portion 64a which has a smaller outside diameter than a distal end side thereof. A distal end portion of a small-diameter inner flexible tube 65, which is inserted in the flexible tube 36, is fitted and fixed in the small-diameter portion 64a. A rear end portion of the inner flexible tube 65 is extended to the rear end side of the flexible tube 36, and is coupled to a radio-frequency knife operation section 66 which is disposed outside the flexible tube 36.

The radio-frequency knife 39 is fixed to a distal end portion of an operation wire 67 which is inserted in the inner flexible tube 65. A tubular stopper-receiving portion 68 is fixed to the periphery of a coupling portion between the radio-frequency knife 39 and the operation wire 67.

The radio-frequency knife operation section 66 includes a circular cylindrical guide member 66a, and a slider 66b which advancibly/retractably slides in the axial direction of the guide member 66a. The control unit 27 of the electronic scalpel is connected to the slider 66b. A rear end portion of the inner flexible tube 65 is fixed to the guide member 66a. A rear end portion of the operation wire 67 is fixed to the slider 66b.

By advancing/retracting the slider 66b in the axial direction relative to the guide member 66a, the radio-frequency knife 39 is axially advanced/retracted. At this time, by pulling the slider 66b to the proximal end side, the radio-frequency knife 39, as shown in FIG. 6B, is stored in a stored position where the radio-frequency knife 39 is retracted from the radio-frequency knife insertion hole 63b of the stopper member 63 to the inside of the distal-end closing portion 63a. By pushing the slider 66b to the distal end side, the radio-frequency knife 39, as shown in FIG. 6A, is projected out of the radio-frequency knife insertion hole 63h of the stopper member 63. At this time, the stopper-receiving portion 68 abuts on the distal-end closing portion 63a of the stopper member 63, and thereby the projection position of the radio-frequency knife 39 is restricted.

The first active mechanism 8 of the first active therapeutic device 6 is provided with a bending section operation mechanism which individually rotates and drives the first bend piece 41 through the fourth bend piece 44 of the bending section 37. The bending section operation mechanism includes four driving motors for pushing and pulling the four pairs of operation wires 51a, 51b, 52a, 52b, 53a, 53b, 54a and 54b, which are associated with the first bend piece 41 through the fourth bend piece 44 which are to be rotated. By individually driving the four driving motors, the four pairs of operation wires 51a, 51b, 52a, 52b, 53a, 53b, 54a and 54b are pushed and pulled.

The second active therapeutic device 7 differs from the first active therapeutic device 6 with respect to the structure of the distal-end therapeutic section 38. Specifically, the second active therapeutic device 7 includes the grasping forceps 40 at the part of the distal-end therapeutic section 38. The grasping forceps 40 is opened/closed by an operation wire (not shown) which is inserted in the inner flexible tube 65. As regards the other parts of the bending section 37 of the multi-joint type bending mechanism of the first active therapeutic device 6, the second active therapeutic device 7 have the same structure. Accordingly, the second active mechanism 9 of the second active therapeutic device 7 has the same structure as the first active mechanism 8 of the first active therapeutic device 6.

The first control output instruction input device 25 is an operation input device which instructs the position and attitude of the first active therapeutic device 6. Similarly, the second control output instruction input device 26 is an operation input device which instructs the position and attitude of the second active therapeutic device 7. The first and second control output instruction input devices 25 and 26 are composed of master-type actuators of a master-slave system, which has the structure of the multi-joint type bending mechanism corresponding to the parts of the bending section 37 of the multi-joint type bending mechanism. The four driving motors of each of the first active mechanism 8 and second active mechanism 9 are individually driven in accordance with the operation of the first, second control output instruction input device 25, 26 of the master-type actuator. At this time, the four pairs of operation wires 51a, 51b, 52a, 52b, 53a, 53b, 54a and 54b, which correspond to the four driving motors of the first active mechanism 8 and second active mechanism 9, are pushed and pulled. Thereby, the first bend piece 41 through the fourth bend piece 44 of the bending section 37 of the multi-joint type bending mechanism of the first active therapeutic device 6 are individually rotated and driven in accordance with the operation of the first control output instruction input device 25. Similarly, the first bend piece 41 through the fourth bend piece 44 of the bending section 37 of the multi-joint type bending mechanism of the second active therapeutic device 7 are individually rotated and driven in accordance with the operation of the second control output instruction input device 26.

Figure 7A:
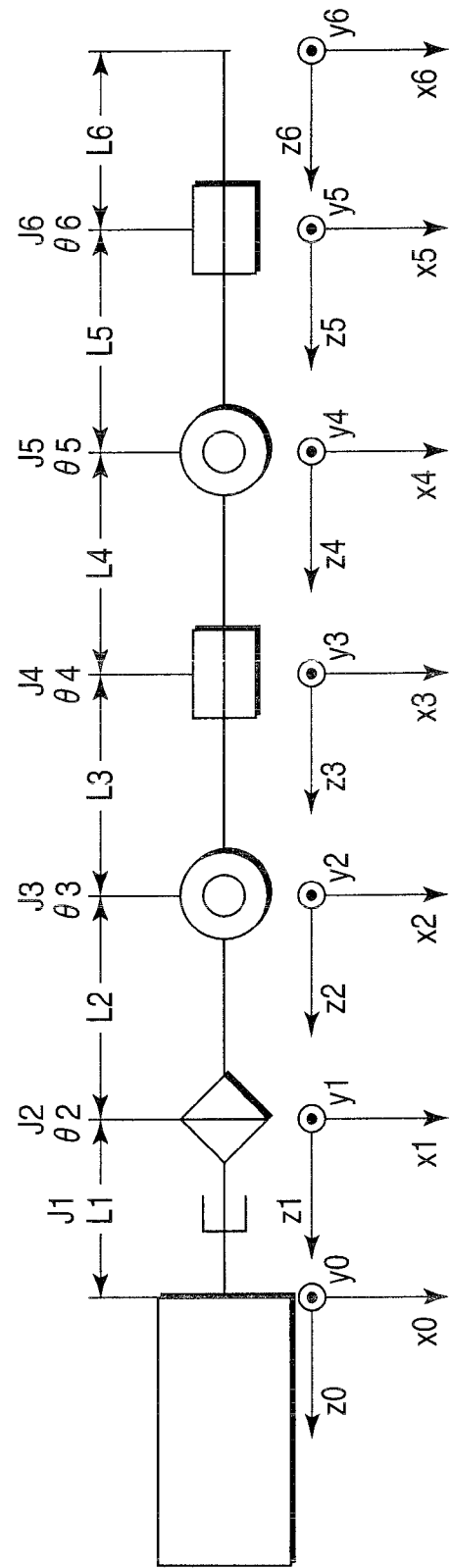
FIG. 7A is a schematic structural view showing the state in which all joints of the multi-joint structure in the bending section of the therapeutic device according to the first embodiment are set in the straight position.
Figure 7B:
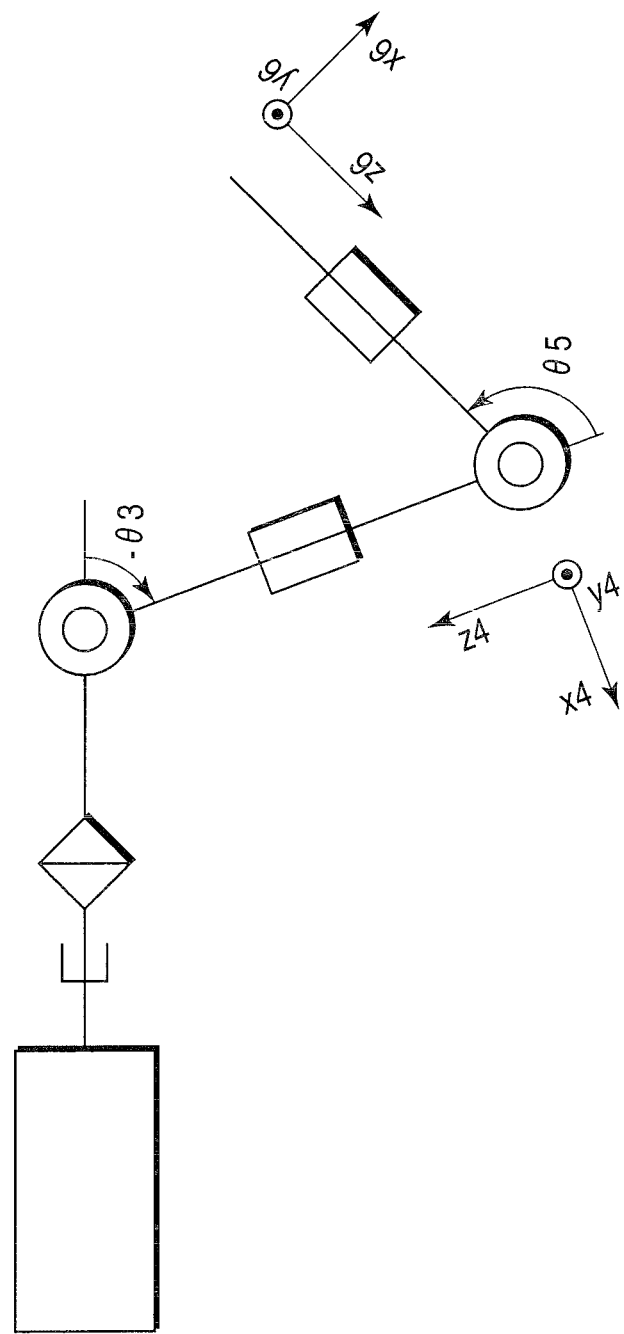
FIG. 7B is a schematic structural view showing an example of the state in which a plurality of joints of the bending section are bent.

FIG. 7A shows a multi-joint structure model of six degrees of freedom in the bending section 37 of the first active therapeutic device 6 of the present embodiment. As shown in FIG. 7A, in the state in which all joint sections of the bending section 37 of the first active therapeutic device 6 are projected from the distal end portion 2a3 of the endoscope 2, the joints, from the one located on the operation section side (proximal end side) to the one located on the distal end side, are successively referred to as J1, J2, J3, J4, J5 and J6. In FIG. 7A, the joint J1 is a mechanism which moves the entirety of the first active therapeutic device 6 in its axial direction, and the joint J2 is a mechanism which moves the entirety of the first active therapeutic device 6 about its axis. The joint J3 corresponds to the fourth joint section A4 in FIG. 5, the joint J4 corresponds to the third joint section A3 in FIG. 5, the joint J5 corresponds to the second joint section A2 in FIG. 5, and the joint J6 corresponds to the first joint section A1 in FIG. 5. FIG. 7A shows the state in which all the joint sections A1 to A4 are straight, and FIG. 7B shows the state in which the fourth joint section A4 (J3) and second joint section A2 (J5), among all the joint sections A1 to A4, are bent.

Since the bending section 37 of the first active therapeutic device 6 includes the plural joint sections A1 to A4, the distal end portion of the first active therapeutic device 6 can be moved to an arbitrary position and attitude, and incision/ablation of a lesion can be performed more easily than in the prior art. In addition, by making the joint structure of the first active therapeutic device 6 equivalently correspond to the joint structure of the first control output instruction input device 25, the surgeon can easily operate the therapeutic device having plural joints.

The first active mechanism 8 and second active mechanism 9 are connected to the therapeutic device control unit 10 over a control cable. As shown in FIG. 3, the therapeutic device control unit 10 includes a control device (therapeutic device operation control means) 69, and locus calculation means 70. The first and second control output instruction input devices 25 and 26, which are operation input devices, and joint selection means 71 are connected to the locus calculation means 70.

The joint selection means 71 selects one or more of joint section that are to be moved, from among the joint sections A1 to A4 of the first, second active therapeutic device 6, 7. Examples of an input method of the joint selection means 71 are as follows.

1. Any of the joint sections A1 to A4 of the first, second active therapeutic device 6, 7 on the display screen of the display device 5, which is of a touch-panel type and displays an endoscopic image, is directly touched by the finger or an input pen, and is thus selected.

2. One of the first and second active therapeutic devices 6 and 7 and the joint number N (1 to the number of joints used) of any one of the joint sections A1 to A4 are input and selected through a keyboard of a personal computer which is attached to the control device 69. In this case, if the selected one of the joint sections A1 to A4 of the first, second active therapeutic device 6, 7 on the display screen of the display device 5 is displayed with a mark or the like, easily understanding is realized.

In the case where the joint selection means 71 is in "joint selection mode off", control is executed by the first control output instruction input device 25 and the second control output instruction input device 26.

The locus calculation means 70 includes locus drawing means. When a driving instruction has been input to any one of the joint sections A1 to A4 of the first, second active therapeutic device 6, 7 by an output signal from the first, second control output instruction input device 25, 26, the locus calculation means 70 calculates the locus of movement of the first, second active therapeutic device 6, 7, on the basis of the joint section, A1 to A4, which has been instructed to operate. At this time, the locus drawing means draws a predetermined locus of movement of the first, second active therapeutic device 6, 7, on the display device 5.

Figure 9:
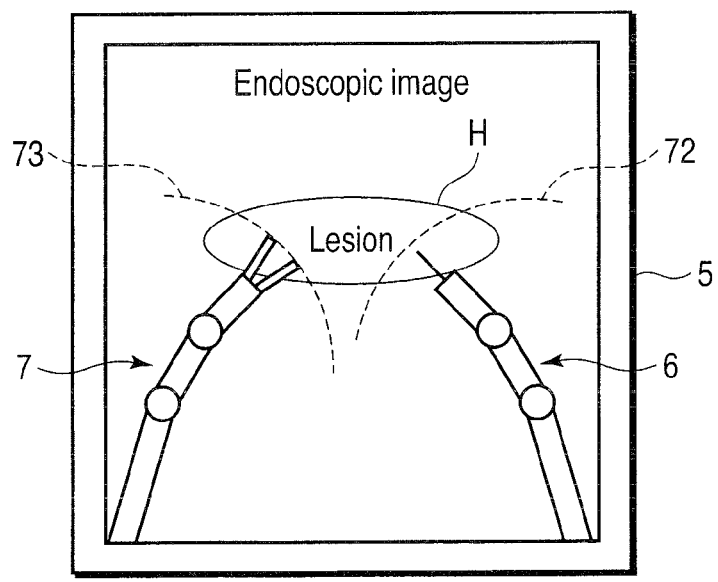
FIG. 9 is a front view showing a display screen of a monitor at a time of operating the therapeutic device of the endoscope apparatus according to the first embodiment.

FIG. 9 shows an example of the display screen which is displayed on the display device 5. An endoscopic image is displayed in front on the screen of the display device 5. The screen of the endoscopic image displays a diseased part (lesion) H or the like in a patient's body, an image of the first active therapeutic device 6, and an image of the second active therapeutic device 7. In this state, in the case where at least one of the first control output instruction input device 25 and the second control output instruction input device 26 is driven, the display device 5 displays a predetermined locus 72 of movement of the distal end of the first active therapeutic device 6, which is calculated and drawn on the basis of any one of the joint sections A1 to A4 of the first active therapeutic device 6, which has been instructed to operate, and a predetermined locus 73 of movement of the distal end of the second active therapeutic device 7, which is calculated and drawn on the basis of any one of the joint sections A1 to A4 of the second active therapeutic device 7, which has been instructed to operate. At this time, the locus 72 of the first active therapeutic device 6 and the locus of 73 of the second active therapeutic device 7 are displayed in different colors on the screen of the display device 5. For example, the locus 72 of the first active therapeutic device 6 is displayed in red, and the locus of 73 of the second active therapeutic device 7 is displayed in green.

The control device 69 causes the first active mechanism 8 or second active mechanism 9 to control the operation of the first active therapeutic device 6 or second active therapeutic device 7 so as to move any one of the joint sections A1 to A4 of the first, second active therapeutic device 6, 7, which has been instructed to operate on the basis of the locus information of the locus that is drawn by the locus drawing means of the locus calculation means 70.

Next, the operation of the present embodiment having the above-described structure is described. When the system of the endoscope apparatus 1 of the present embodiment is used, the insertion section of the endoscope 2 is inserted in advance in the patient's body cavity. The distal end portion of the insertion section of the endoscope 2 is inserted to a position near the diseased part (lesion) H or the like in the patient's body. At this time, image data that is captured by the image pickup unit of the endoscope 2 is image data of the lesion or the like in the body cavity, which is captured by the image pickup element such as a CCD. An image pickup signal which is obtained by the image pickup unit of the endoscope 2 is sent to the display processor 4 over a connection cable, and converted to a video signal. By the video signal, the display device 5 displays an observation image including the lesion H and the neighborhood thereof, which is captured by the endoscope 2.

In this state, the first active therapeutic device 6 is inserted in one therapeutic device insertion channel 33a of the endoscope 2, and the second active therapeutic device 7 is inserted in the other therapeutic device insertion channel 33b. As shown in FIG. 4A, the first and second active therapeutic devices 6 and 7, which are inserted in the therapeutic device insertion channels 33a and 33b, are projected from the opening portions of the therapeutic device insertion channels 33a and 33b of the distal-end rigid portion 2a3. Thereby, as shown in FIG. 9, the endoscopic image of the display device 5 displays the lesion H or the like in the body cavity and the distal end portions of the first active therapeutic device 6 and second active therapeutic device 7. At this time, in the endoscopic image of the display device 5, the distal end portions of the first active therapeutic device 6 and second active therapeutic device 7 are set in the state in which a plurality of joints, for instance, the first joint section A1 and second joint section A2, are displayed.

Figure 8:
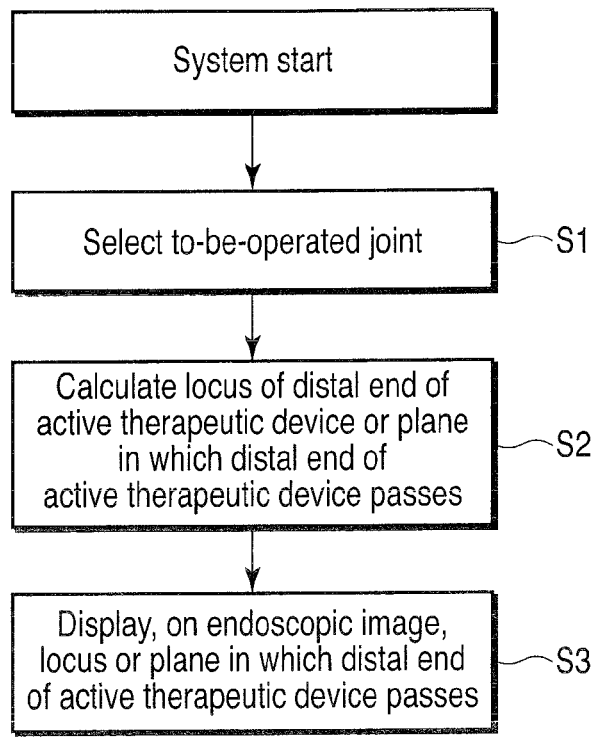
FIG. 8 is a flow chart for explaining the operation of the endoscope apparatus according to the first embodiment.

Thereafter, an operation is performed to guide the first active therapeutic device 6 or second active therapeutic device 7 to a desired position. At the time of this operation, the first, second control output instruction input device 25, 26 of the therapeutic device operation unit 21 is used. Then, an operation illustrated in a flow chart of FIG. 8 is performed.

To begin with, after the system is started, in the first step S1, any one of the joint sections A1 to A4 of the first, second active therapeutic device 6, 7, which is to be operated, is selected by the joint selection means 71.

In the next step S2, the locus calculation means 70 calculates a predetermined locus of movement of the distal end of the first active therapeutic device 6, or a predetermined locus of movement of the distal end of the second active therapeutic device 7. At this time, the locus calculation means 70 may calculate a plane (see FIG. 13) in which the distal end of the first, second active therapeutic device 6, 7 passes, instead of the predetermined locus 72, 73 of movement of the distal end of the first, second active therapeutic device 6, 7.

Subsequently, in the next step S3, the locus drawing means of the locus calculation means 70 outputs a control signal to the display processor 4. Thereby, the display processor 4 draws, on the display device 5, at least one of the predetermined locus 72 of movement of the distal end of the first active therapeutic device 6, which is displayed in red and calculated on the basis of any one of the joint sections A1 to A4 of the first active therapeutic device 6, which has been instructed to operate, and the predetermined locus 73 of movement of the distal end of the second active therapeutic device 7, which is displayed in green and calculated on the basis of any one of the joint sections A1 to A4 of the second active therapeutic device 7, which has been instructed to operate. FIG. 9 shows the example in which the second joint section A2 of the first active therapeutic device 6 and the first joint section A1 of the second active therapeutic device 7 are selected as to-be-operated joints. At this time, the plane (see FIG. 13) in which the distal end of the first, second active therapeutic device 6, 7 passes may drawn on the display device 5, instead of the predetermined locus 72, 73 of movement of the distal end of the first, second active therapeutic device 6, 7.

According to the above-described structure, the following advantageous effects are obtained. Specifically, in the system of the endoscope apparatus 1 of the present embodiment, in the case where the bending section 37 of the first active therapeutic device 6 or the second active therapeutic device 7 is operated, the locus calculation means 70 calculates the locus 72 of movement of the distal end portion of the first active therapeutic device 6 or the locus 73 of movement of the distal end portion of the second active therapeutic device 7, on the basis of the joint section which has been instructed to operate by the first, second control output instruction input device 25, 26. On the basis of the calculation result of the locus calculation means 70, the control device 69 causes the first active mechanism 8 or second active mechanism 9 to control the operation of the first active therapeutic device 6 or second active therapeutic device 7 so as to move any one of the joint sections A1 to A4 of the first, second active therapeutic device 6, 7, which has been instructed to operate. Thereby, the locus 72, 73 of movement of the distal end portion of the first, second active therapeutic device 6, 7, which is based on the joint information of the arbitrarily selected joint, can be calculated, and the driving control of the first, second active therapeutic device 6, 7, can be executed on the basis of the locus 72, 73. The first, second active therapeutic device 6, 7, which is the multi-joint therapeutic device, can efficiently be driven. Thus, even in the case where the active mechanism for moving the first, second active therapeutic device 6, 7, has six degrees of freedom, control can be executed to move only an arbitrarily selected one (or more) of the joint sections A1 to A4 of the first, second active therapeutic device 6, 7, with respect to an operation which can be realized with use of only one joint. As a result, even in the case where the active mechanism for moving the first, second active therapeutic device 6, 7, has six degrees of freedom, the number of joints, which are used in the operation of the therapeutic device, can be limited depending on conditions, and, unlike the prior art, there is no need to perform the operations of joints by controlling the positions and attitudes of all joints. Hence, the accumulated errors of the respective joints that are used and the decrease in energy efficiency can be reduced. Therefore, the operational efficiency and positional precision of the first, second active therapeutic device 6, 7 can be improved.

In addition, in the present embodiment, when the driving instruction is input by the first, second control output instruction input device 25, 26, the locus drawing means of the locus calculation means 70 draws the locus 72, 73 of movement of the distal end portion of the first, second active therapeutic device 6, 7 on the endoscopic image of the display device 5, on the basis of any one of the joint sections A1 to A4 of the first, second active therapeutic device 6, 7, which has been instructed to operate. Thereby, while viewing the locus 72, 73 of movement of the distal end portion of the first, second active therapeutic device 6, 7 on the endoscopic image of the display device 5, an operation can be executed to move the distal end portion of the first, second active therapeutic device 6, 7 to a target location, such as the lesion H or the like in the body cavity. Therefore, an operation can easily be performed to move the distal end portion of the first, second active therapeutic device 6, 7 to a target location, such as the lesion H or the like in the body cavity.

Figure 10:
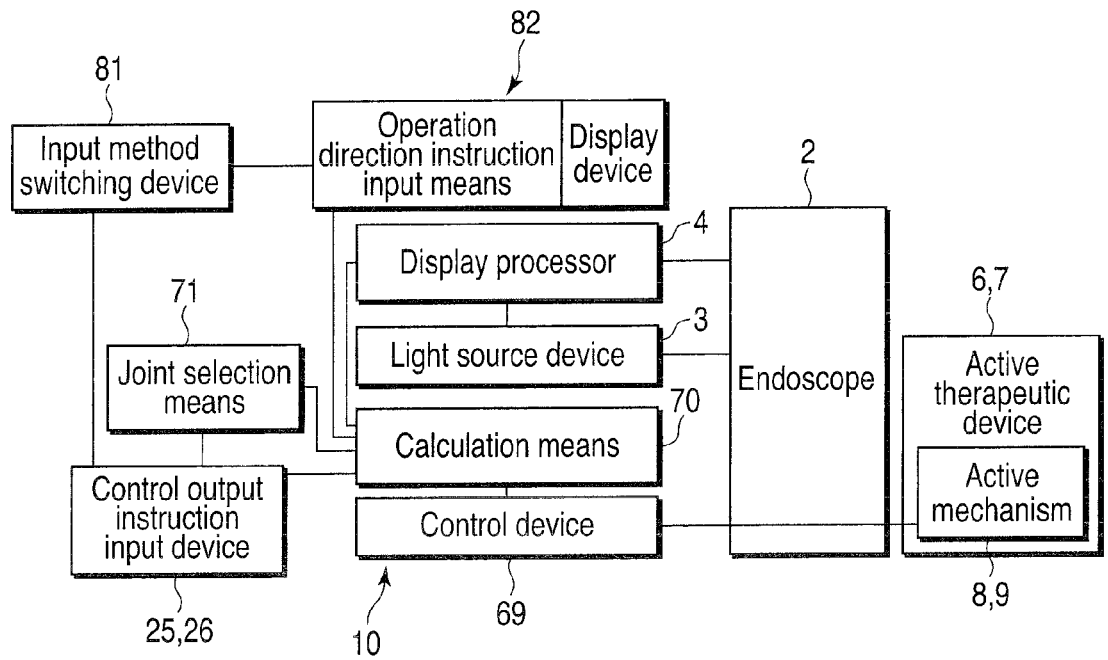
FIG. 10 is a block diagram of the entire system of an endoscope apparatus according to a second embodiment of the present invention.
Figure 11:
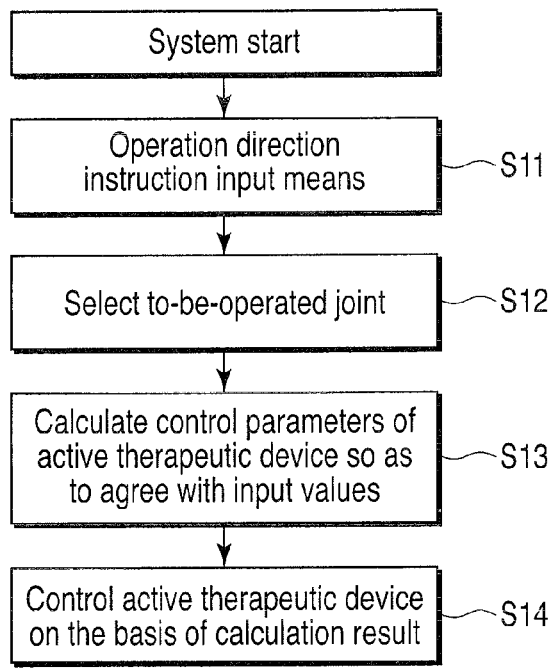
FIG. 11 is a flow chart for explaining the operation of the endoscope apparatus according to the second embodiment.
Figure 12:
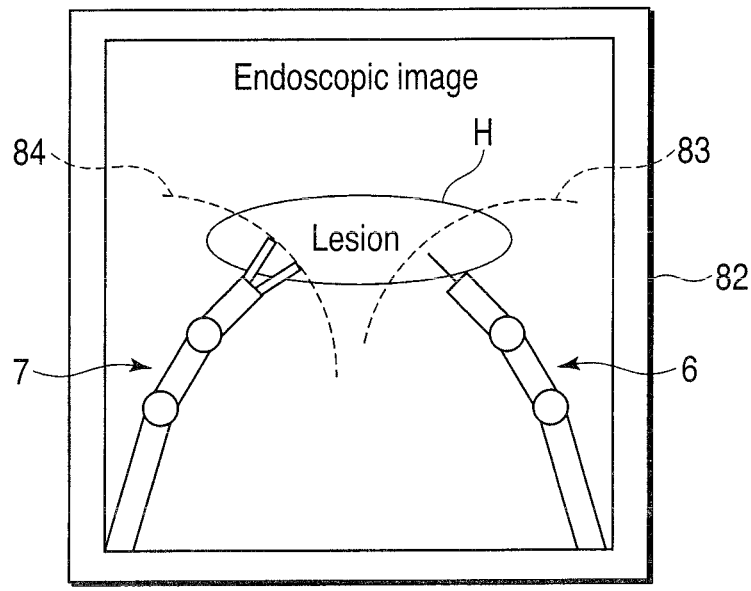
FIG. 12 is a front view showing a display screen of a monitor at a time of operating the therapeutic device of the endoscope apparatus according to the second embodiment.

FIG. 10 to FIG. 12 show a second embodiment of the present invention. In the second embodiment, the structure of the system of the endoscope apparatus 1 of the first embodiment (see FIG. 1 to FIG. 9) is altered in the following manner.

In the present embodiment, as shown in FIG. 10, operation direction instruction input means 82 is connected to the locus calculation means 70 of the system of the first embodiment. The operation direction instruction input means 82 includes, for example, a touch-panel type display device 82a shown in FIG. 12. Loci 83 and 84 of movement of the first active therapeutic device 6 and second active therapeutic device 7 are directly input by the finger or an input device, such as a pen, on an endoscopic image which is displayed on the touch-panel type display device 82a. The loci 83 and 84, which are indicated by broken lines in the image, are input.

An input direction switching device 81 is connected to the operation direction instruction input means 82. The input direction switching device 81 is also connected to the first and second control output instruction input devices 25 and 26. The input direction switching device 81 sets in the locus calculation means 70 the input mode of moving the first active therapeutic device 6 and second active therapeutic device 7. In the present embodiment, the input direction switching device 81 executes selective switching between a master-slave mode in which the first and second control output instruction input devices 25 and 26 of the therapeutic device operation unit 21 are used, and an operation direction instruction input mode in which the operation direction instruction input means 82 is used.

Next, the operation of the embodiment having the above-described structure is described. As shown in FIG. 12, when the system of the endoscope apparatus 1 of the present embodiment is used, the endoscopic image of the display device 82a displays the lesion H or the like in the body cavity and the distal end portions of the first active therapeutic device 6 and second active therapeutic device 7. At this time, in the endoscopic image of the display device 5, the distal end portions of the first active therapeutic device 6 and second active therapeutic device 7 are set in the state in which a plurality of joints, for instance, the first joint section A1 and second joint section A2, are displayed.

Thereafter, an operation is performed to guide the first active therapeutic device 6 or second active therapeutic device 7 to a desired position. At the time of this operation, the input direction switching device 81 selects one of the master-slave mode in which the first and second control output instruction input devices 25 and 26 of the therapeutic device operation unit 21 are used, and the operation direction instruction input mode in which the operation direction instruction input means 82 is used.

In the case where the master-slave mode is selected by the input direction switching device 81, the same operation as in the first embodiment is performed. In the case where the input direction switching device 81 effects switching to the operation direction instruction input mode in which the operation direction instruction input means 82 is used, an operation illustrated in FIG. 11 is performed.

To begin with, after the system is started, in the first step S11, the operation direction instruction input means 82 is used. At this time, loci 83 and 84 of movement of the first active therapeutic device 6 and second active therapeutic device 7 are directly input by the finger or an input device, such as a pen, on an endoscopic image which is displayed on the display device 82a of the operation direction instruction input means 82. Specifically, the operator inputs the loci 83 and 84, which are indicated by broken lines in the image, in directions in which the distal end portions of the first active therapeutic device 6 and second active therapeutic device 7 are to be moved, so that therapeutic treatment of the lesion H may be performed.

In the next step S12, as in the first embodiment, any one of the joint sections A1 to A4 of the first, second active therapeutic device 6, 7, which is to be operated, is selected by the joint selection means 71.

Subsequently, in the next step S13, the locus calculation means 70 calculates control parameters of the predetermined locus 83 of movement of the distal end of the first active therapeutic device 6 or the predetermined locus 84 of movement of the distal end of the second active therapeutic device 7, so that the control parameters correspond to the input values of the locus 83, 84.

In the next step S14, the control device 69 controls the operation of the first, second active therapeutic device 6, 7, on the basis of the calculation result of the calculation means 70. At this time, a plane (see FIG. 13) in which the distal end of the first, second active therapeutic device 6, 7 passes may be calculated instead of the predetermined locus 83, 84 of movement of the distal end of the first, second active therapeutic device 6, 7.

According to the above-described structure, the following advantageous effects are obtained. Specifically, in the system of the endoscope apparatus 1 of the present embodiment, in the case where the bending section 37 of the first active therapeutic device 6 or the second active therapeutic device 7 is operated, the input direction switching device 81 can select one of the master-slave mode in which the first and second control output instruction input devices 25 and 26 of the therapeutic device operation unit 21 are used, and the operation direction instruction input mode in which the operation direction instruction input means 82 is used. In the case where the input direction switching device 81 effects switching to the operation direction instruction input mode in which the operation direction instruction input means 82 is used, the loci 83 and 84 of movement of the first active therapeutic device 6 and second active therapeutic device 7 are directly input by the finger or an input device, such as a pen, on the endoscopic image which is displayed on the display device 82*a* of the operation direction instruction input means 82.

Thereafter, on the basis of the input by the operation direction instruction input means 82, any one of the joint sections A1 to A4 of the first, second active therapeutic device 6, 7, which is to be operated, is selected by the joint selection means 71. At this time, on the basis of the joint section that has been instructed to operate, the locus calculation means 70 calculates the control parameters so as to correspond to the input values of the loci 83, 84 in the directions in which the distal ends of the first active therapeutic device 6 and second active therapeutic device 7 are to be moved. On the basis of the calculation result by the locus calculation means 70, the control device 69 causes the first active mechanism 8 or second active mechanism 9 to control the operation of the first active therapeutic device 6 or second active therapeutic device 7 so as to move any one of the joint sections A1 to A4 of the first, second active therapeutic device 6, 7, which has been instructed to operate.

Thereby, in the present embodiment, the operation of the first, second active therapeutic device 6, 7 can be controlled by directly inputting the loci 83 and 84 of movement of the first active therapeutic device 6 and second active therapeutic device 7 by the finger or an input device, such as a pen, on the endoscopic image which is displayed on the display device 82*a* of the operation direction instruction input means 82, and the first, second active therapeutic device 6, 7, which is the multi-joint therapeutic device, can efficiently be driven. Thus, even in the case where the active mechanism for moving the first, second active therapeutic device 6, 7, has six degrees of freedom, control can be executed to move only an arbitrarily selected one (or more) of the joint sections A1 to A4 of the first, second active therapeutic device 6, 7, with respect to an operation which can be realized with use of only one joint. As a result, even in the case where the active mechanism for moving the first, second active therapeutic device 6, 7, has six degrees of freedom, the number of joints, which are used in the operation of the therapeutic device, can be limited depending on conditions, and, unlike the prior art, there is no need to perform the operations of joints by controlling the positions and attitudes of all joints. Hence, the accumulated errors of the respective joints that are used and the decrease in energy efficiency can be reduced. Therefore, the operational efficiency and positional precision of the first, second active therapeutic device 6, 7 can be improved.

Furthermore, in the present embodiment, on the basis of the input of the operation direction instruction input means 82, the control device 69 executes control to establish agreement between the direction of operation of the distal end portion of the first, second active therapeutic device 6, 7, the joint section which is selected by the working joint selection means 71 and the locus of the distal end portion of the first, second active therapeutic device 6, 7 at this time, in association with the other joint sections of the first, second active therapeutic device 6, 7 which are not selected by the working joint selection means 71. Accordingly, the number of joints, which are used in the operation of the first, second active therapeutic device 6, 7, can be limited depending on conditions, and thereby the operational efficiency and positional precision of the first, second active therapeutic device 6, 7 can be improved.

Figure 13:
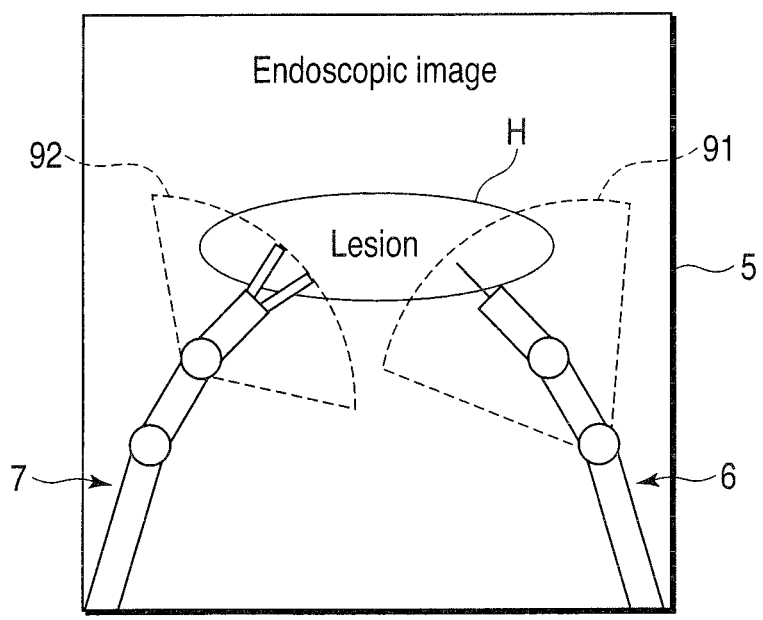
FIG. 13 is a front view showing a modification in which the display screen displays a plane in which distal end portions of therapeutic devices pass at a time of operating the therapeutic device of the endoscope apparatus according to the first embodiment.

FIG. 13 shows a modification of the endoscope apparatus 1 according the above-described first embodiment. In the structure of the first embodiment, when the operations of the first active therapeutic device 6 and second active therapeutic device 7 are controlled, the locus calculation means 70 calculates the predetermined locus 72 of movement of the distal end portion of the first active therapeutic device 6 or the predetermined locus 73 of movement of the distal end portion of the second active therapeutic device 7. In the structure of the present modification, the locus calculation means 70 calculates a plane 91, 92, in which the distal end of the first, second active therapeutic device 6, 7 passes, and the plane 91, 92, in which the distal end of the first, second active therapeutic device 6, 7 passes, is displayed on the display screen of the display device 5, 82*a*. With this modification, the same advantageous effects as in the first embodiment can be obtained.

Figure 14:
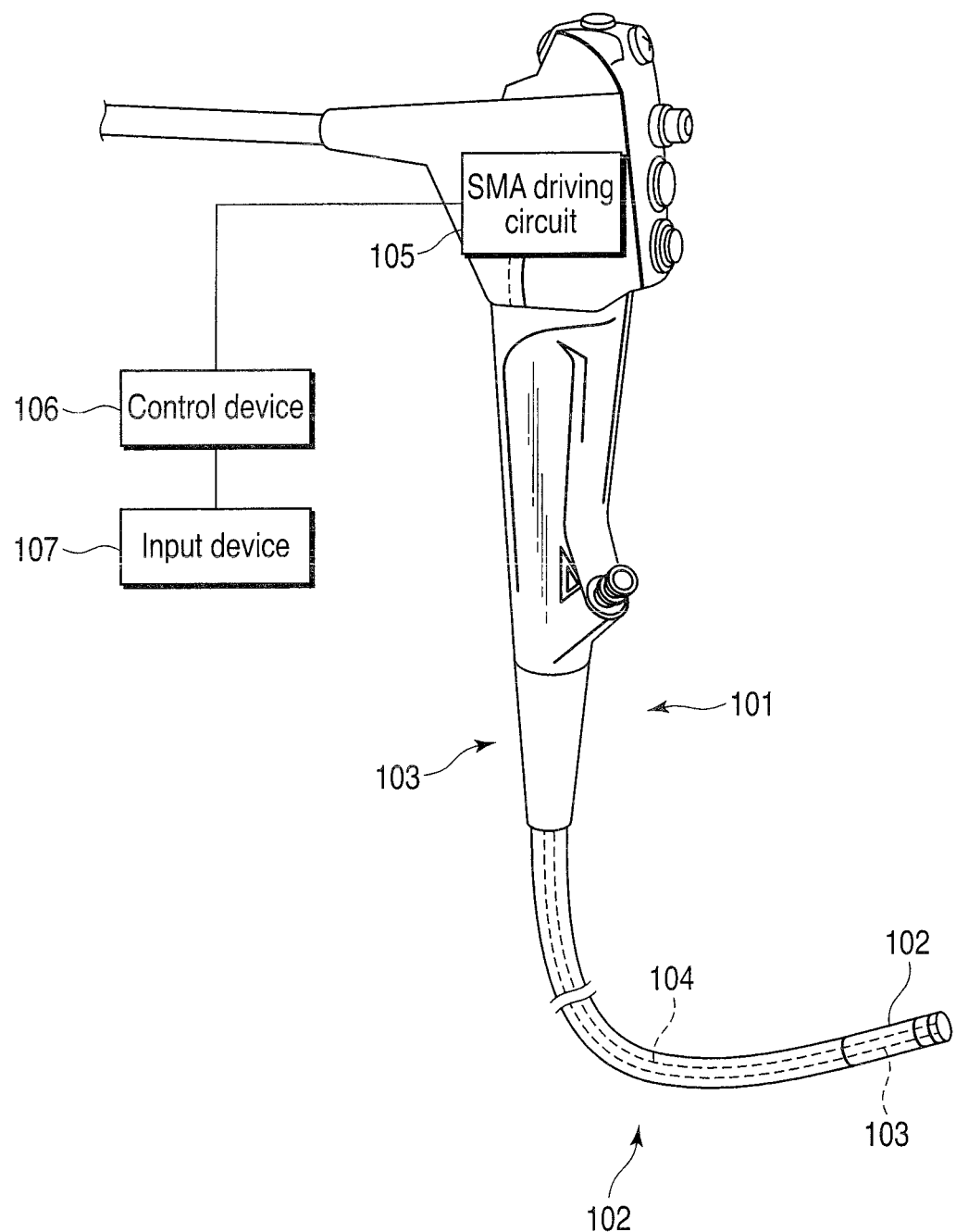
FIG. 14 is a perspective view of an endoscope, for describing an endoscope apparatus according to a third embodiment of the present invention.

FIG. 14 shows an example in which a shape-memory alloy (SMA) wire 103 is used as the driving mechanism of a bending section 102*b* of an insertion section 102 of an endoscope 101. Numeral 102*a* denotes a flexible tube portion of the insertion section 102, and numeral 102*c* denotes a distal end portion. The SMA wire 103 is connected to a proximal-side SMA driving circuit 105 via an electrically conductive lead wire 104 such as copper wire. A control device 106 is connected to the SMA driving circuit 105. An input device 107 is connected to the control device 106.

When power is turned off, the SMA wire 103 is formed in a straight shape with a fixed length. At this time, the bending section 102*b* of the endoscope 101 is held in a straight non-bent shape (initial shape).

When electric current is supplied via the lead wire 104, the SMA wire 103 is heated by electric conduction. At this time, the shape of the SMA wire 103 is deformed, for example, in a contracted shape, and the bending section 102b of the endoscope 101 is bend-operated in accordance with the deformation of the SMA wire 103.

Such structure (third embodiment) may be adopted that the SMA wire 103 is connected to the distal end of each of the operation wires of the four wire units 51 to 54 of the bending section 37 of the multi-joint type bending mechanism of the first active therapeutic device 6 and second active therapeutic device 7 of the endoscope 1 according to the first embodiment (see FIG. 1 to FIG. 9). In this case, the four wire units 51 to 54 are individually and independently driven in accordance with the deformation of the SMA wire 103 of each operation wire of the four wire units 51 to 54 of the bending section 37, and thereby the first bend piece 41 through the fourth bend piece 44 can individually be bent. In the meantime, an actuator, such as an artificial muscle, may be used for the SMA wire 103 of this embodiment.

FIG. 15 shows a fourth embodiment of the present invention. In this embodiment, a display screen 111 of the display device 5 of the endoscope apparatus 1 according to the first embodiment (see FIG. 1 to FIG. 9) is altered as shown in FIG. 15.

Specifically, the display screen 111 of the display device 5 of the present embodiment is provided with two (first and second) display regions 112 and 113. The first display region 112 displays an endoscopic image, which is similar to the image displayed on the display screen of the display device 5 of the first embodiment. The second display region 113 includes an input method display region 113a which displays an input method of the joint selection means 71, and a joint selection state display region 113b which displays a joint selection state.

The input method display region 113a displays the kind of input method of the joint selection means 71, and a selection result thereof. For example, as the kinds of input method of the joint selection means 71, three items, "1: touch panel", "2: mouse" and "3: other device", are displayed. In addition, in FIG. 15, as regards the section result, "2: mouse" is selected as the input method.

The joint selection state display region 113b displays ON/OFF of the joint selection mode, and a joint to be controlled. In this case, easy understanding is realized if a mark or the like is added to a selected one of the joint sections A1 to A4 of the first, second active therapeutic device 6, 7 on the display screen of the joint selection state display region 113b.

Needless to say, the present invention is not limited to the above-described embodiments, and various modifications may be made without departing from the spirit of the invention.

Next, other characteristic technical matters of the present invention are noted below.

NOTE (Item 1) An endoscope apparatus including an endoscope which captures an image in a subject; a therapeutic device which is composed of a plurality of joints and is inserted in the subject via a channel of the endoscope; operation means for operating the therapeutic device; locus calculation means for calculating a locus of movement of the therapeutic device on the basis of a joint which is instructed to operate; and therapeutic device operation control means for controlling an operation of the therapeutic device by the operation means on the basis of a calculation result by the locus calculation means.

(Item 2) An endoscope apparatus including an endoscope which captures an image in a subject; a therapeutic device which is composed of a plurality of joints and is inserted in the subject via a channel of the endoscope; operation means for operating the therapeutic device; working joint selection means for selecting a to-be-operated one of the plurality of joints; locus calculation means for calculating a locus of movement of the therapeutic device on the basis of joint information of the joint which is selected by the working joint selection means; and therapeutic device operation control means for controlling an operation of the therapeutic device by the operation means on the basis of a calculation result by the locus calculation means.

(Item 3) An endoscope apparatus including an endoscope which captures an image in a subject; display means for displaying the captured image; a therapeutic device which is composed of a plurality of joints and is inserted in the subject via a channel of the endoscope; operation means for operating the therapeutic device; locus drawing means for drawing a predetermined locus of movement of the therapeutic device on the display means; and therapeutic device operation control means for controlling an operation of the therapeutic device by the operation means with a joint, which is instructed to operate, on the basis of locus information of the locus which is drawn by the locus drawing means.

(Item 4) An endoscope apparatus including an endoscope which captures an image in a subject; display means for displaying the captured image; a therapeutic device which is composed of a plurality of joints and is inserted in the subject via a channel of the endoscope; operation means for operating the therapeutic device; locus drawing means for drawing a predetermined locus of movement of the therapeutic device on the display means; working joint selection means for selecting a to-be-operated one of the plurality of joints on the basis of locus information of the locus which is drawn by the locus drawing means; and therapeutic device operation control means for controlling an operation of the therapeutic device by the operation means on the basis of joint information of the joint which is selected by the working joint selection means.

(Item 5) An endoscope therapeutic system including an endoscope which observes an inside of the body; a display processor for processing an image which is captured by the endoscope; a display device for displaying the image which is captured by the endoscope; a light source device for effecting image pickup by the endoscope; an active therapeutic device for performing both or one of observation and therapeutic treatment in the body; an active mechanism for moving the active therapeutic device; a control device for controlling the active mechanism; and a control output instruction input device for inputting an instruction of an operator to the control device, wherein the active therapeutic device includes one or more joints, the system includes joint selection means for selecting the joint, the control device sets, as an object of operation, the joint that is selected by the joint section means or a predetermined joint, and includes calculation means for calculating a locus which is drawn by a distal end of the active therapeutic device when the joint is operated, or a plane in which the distal end of the active therapeutic device passes, and the locus which is drawn by the distal end of the active therapeutic device or the plane in which the distal end of the active therapeutic device passes is displayed on an endoscopic image on the basis of a calculation result by the calculation means.

(Item 6) The endoscope therapeutic system according to item 5, wherein the joint selection means is a switching device for selecting one or more of the joints of the active mechanism.

(Item 7) The endoscope therapeutic system according to item 5, further including operation direction instruction input means for instructing and inputting an operation direction of the distal end of the active therapeutic device on the endoscopic image which is displayed on a display screen of the display device, wherein the control device controls the active mechanism on the basis of an input of the operation direction instruction input means.

(Item 8) The endoscope therapeutic system according to item 7, wherein the operation direction instruction input means is a 3-D input device.

(Item 9) The endoscope therapeutic system according to item 7, including the operation direction instruction input means and an input method switching device for switching an input mode of the control output instruction input device.

(Item 10) The endoscope therapeutic system according to item 7, wherein the control device executes control to establish agreement between the operation direction of the distal end of the active therapeutic device which is input by the operation direction instruction input means, the joint which is selected by the selection means and the locus of the distal end of the active therapeutic device at this time or the plane in which the distal end of the active therapeutic device passes, in association with the other joints of the active therapeutic device which are not selected by the joint selection means.

The present invention is effective in a technical field of a control apparatus which controls the operation of a therapeutic device when diagnosis or therapeutic treatment of a lesion in a body cavity is performed by using the therapeutic device which is inserted in a channel of an endoscope, and in a technical field of manufacturing and using the control apparatus of the therapeutic device.

What is claimed is:

1. An endoscope apparatus comprising:
    an endoscope which includes a channel and an image pickup unit configured to capture an image;
    a display which displays the captured image;
    a therapeutic device which includes an insertion section configured to be inserted in a subject via the channel of the endoscope, the insertion section including a plurality of joint sections which are capable of being individually operated;
    an instruction input unit configured to receive an instruction for operating the therapeutic device, the instruction including a selection of at least driving one of the joint sections displayed on the display;
    a locus calculation unit which calculates a locus along which the therapeutic device is capable of moving when the selected joint section is operated on the basis of the instruction, when the operation instruction is input by the instruction input unit;
    a locus drawing unit which superimposes the locus on the image captured by the image pickup unit and displayed on the display; and
    a therapeutic device control unit which controls an operation of the selected joint section configured to cause the therapeutic device to move along the locus calculated by the locus calculation unit and displayed by the locus drawing unit,
    wherein the instruction input unit is capable of switching between a joint selection mode which instructs the selection of at least driving one of the joint sections, and a joint selection mode off, which does not instruct the selection of at least driving one of the joint sections, the instruction input unit further comprising a control output instruction device including a joint structure equivalently corresponding to the joint sections of the therapeutic device, and
    when the instruction input unit is switched to the joint selection mode off, a master-slave control of the therapeutic device is executed by the control output instruction device, and when the instruction input unit is switched to the joint selection mode, a control is executed by the therapeutic device control unit.

2. The endoscope apparatus according to claim 1, wherein the instruction input unit includes a working joint selection section configured to input a selection of said at least driving one of the joint sections, and
    the locus calculation unit calculates the locus on the basis of joint information of the selected joint section.

3. The endoscope apparatus according to claim 2, wherein the working joint selection section includes a switching device configured to select said at least driving one of the joint sections.

4. The endoscope apparatus according to claim 1, wherein the locus calculation unit includes a calculation section for calculating at least one of a locus of a point along which a distal end portion of the therapeutic device is capable of moving and a plane in which the distal end portion of the therapeutic device is capable of passing on the basis of the instruction, and
    the locus drawing unit superimposes one of the locus and the plane on the image captured by the image pickup unit and displayed on the display.

5. The endoscope apparatus according to claim 1, wherein the instruction input unit includes an operation direction instruction input section configured to input an operation direction of a distal end portion of the therapeutic device, and
    the therapeutic device control unit controls the operation of the selected joint section on the basis of the operation direction.

6. The endoscope apparatus according to claim 2, wherein the working joint selection section includes a touch panel which is arranged on the display, and
    the locus calculation unit selects at least driving one of the joint sections on the basis of a touch point on the touch panel, the touch point corresponding to the image of the joint sections displayed on the display.

7. The endoscope apparatus according to claim 2, wherein each of the joint sections has a joint number, and
    the locus calculation unit selects said at least driving one of the joint sections on the basis of the joint number which is input by the working joint selection section.

8. The endoscope apparatus according to claim 1, wherein the joint selection mode further includes an operation direction instruction input mode, and
    when the instruction input unit is in the operation direction instruction input mode, locus to drive the therapeutic device is input on the display prior to the selection of at least driving one of the joint sections displayed on the display.

9. The endoscope apparatus according to claim 8, wherein the locus calculation unit is configured to calculate a control parameter to drive distal end of the therapeutic device so as to correspond to the locus input on the display after the selection of at least driving one of the joint sections displayed on the display, and the therapeutic device control unit is configured to control an operation of the therapeutic device on the basis of the control parameter.

\* \* \* \* \*